(12) United States Patent
Bapat et al.

(10) Patent No.: US 9,428,461 B2
(45) Date of Patent: Aug. 30, 2016

(54) PROCESS FOR THE PREPARATION OF A BENZAZEPINE DERIVATIVE

(71) Applicant: RPG Life Sciences Limited, Mumbai (IN)

(72) Inventors: Uday Rajaram Bapat, Navi Mumbai (IN); Ranjan Prasad Srivastava, Navi Mumbai (IN); Pravin Chaburao Kolhe, Navi Mumbai (IN); Pravin Ganpat Talekar, Navi Mumbai (IN)

(73) Assignee: RPG LIFE SCIENCES LIMITED, Mumbai (IN)

( * ) Notice: Subject to any disclaimer, the term of this patent is extended or adjusted under 35 U.S.C. 154(b) by 58 days.

(21) Appl. No.: 14/518,942

(22) Filed: Oct. 20, 2014

(65) Prior Publication Data

US 2015/0112059 A1    Apr. 23, 2015

(30) Foreign Application Priority Data

Oct. 21, 2013   (IN) .......................... 3296/MUM/2013

(51) Int. Cl.
*C07D 223/16*    (2006.01)

(52) U.S. Cl.
CPC .................................. *C07D 223/16* (2013.01)

(58) Field of Classification Search
CPC ....................................................... C07D 223/16
USPC ........................................................ 540/593
See application file for complete search history.

(56) References Cited

U.S. PATENT DOCUMENTS 5,258,510 A    11/1993   Ogawa et al.
8,273,735 B2   9/2012    Torisawa et al.
8,501,730 B2   8/2013    Torisawa et al.

OTHER PUBLICATIONS

Kondo, et al., 7-Chloro-5-hydroxy-1-[2-methyl-4-(2-methylbenzoyl-amino)benzoyl]-2,3,4,5-tetrahydro-1H-1-benzazepine (OPC-41061): A Potent, Orally Active Nonpeptide Arginine Vasopressin $V_2$ Receptor Antagonist, Bioorganic & Medicinal Chemistry, 1999, 7:1743-1754.

*Primary Examiner* — Brenda Coleman
(74) *Attorney, Agent, or Firm* — Blank Rome LLP

(57) ABSTRACT

Provided is an industrially scalable process for the preparation of a benzazepine derivative, namely, 7-chloro-5-hydroxy-1-[2-methyl-4-(2-methyl benzoyl amino) benzoyl]-2,3,4,5-tetrahydro-1H-1-benzazepine (generically referred as Tolvaptan).

8 Claims, No Drawings

PROCESS FOR THE PREPARATION OF A BENZAZEPINE DERIVATIVE

This application claims the benefit of Indian Patent Application No. 3296/MUM/2013, filed Oct. 21, 2013, which is hereby incorporated by reference.

FIELD OF THE INVENTION

The present invention, in general, relates to the field of process chemistry and more particularly, an industrially scalable process for the preparation of benzazepine derivative 7-chloro-5-hydroxy-1-[2-methyl-4-(2-methyl benzoyl amino) benzoyl]-2,3,4,5-tetrahydro-1H-1-benzazepine (generically referred as Tolvaptan) with more than 80% product yield.

BACKGROUND OF THE INVENTION

Tolvaptan, chemically 7-chloro-5-hydroxy-1-[2-methyl-4-(2-methyl benzoyl amino) benzoyl]-2,3,4,5-tetrahydro-1H-1-benzazepine and structurally represented by Formula 1, (Formula 1)

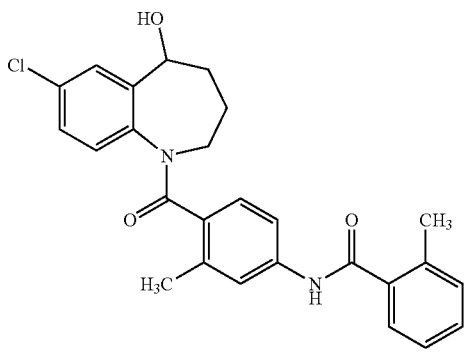

is disclosed in U.S. Pat. No. 5,258,510 (Ogawa et al.) and belongs to a class of arginine vasopression receptor 2 antagonist used to treat hyponatremia associated with congestive heart failure, cirrhosis, and the syndrome of inappropriate antidiuretic hormone (SIADH). Globally, Tolvaptan is sold by Otsuka Pharmaceutically Co. under the trade name Samsca®.

According to Ogawa et al., Tolvaptan is purified using column chromatography, which necessitates huge volumes of solvents that is commercially and industrially not a viable technique.

A process for preparing Tolvaptan of Formula 1 from starting material 7-chloro-1-[2-methyl-4-(2-methyl benzoyl amino) benzoyl]-5-oxo-2,3,4,5-tetrahydro-1H-1-benzazepine of Formula 2 using hydrogenating agent is disclosed in U.S. Pat. Nos. 8,273,735 and 8,501,730 (Torisawa et al.), as shown in the scheme below:

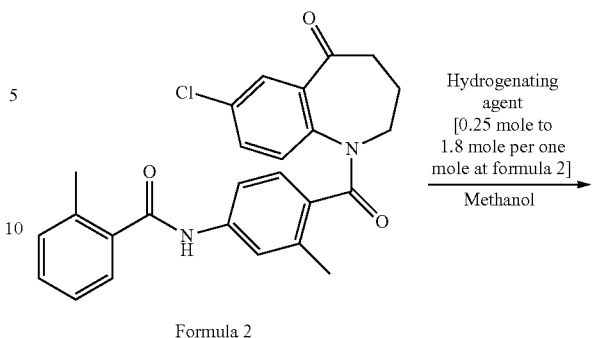

Formula 2

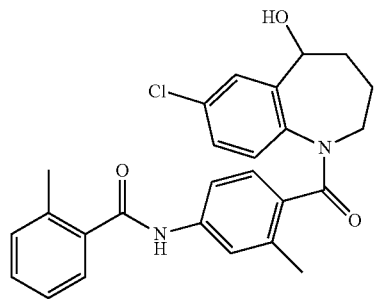

Formula 1

The hydrogenating agent used in this process is in an amount of 0.25 to 1 moles and more preferably 0.25 to 0.5 moles per 1 mole of starting material. This process limits the quantity of hydrogenating agent from 0.25 to 1 mole per 1 mole of starting material to minimize the generation of dehalogenated side product, 5-hydroxy-1-[2-methyl-4-(2-methyl benzoylamino) benzoyl]-2,3,4,5-tetrahydro-1H-1-benzazepine of Formula 3.

(Formula 3)

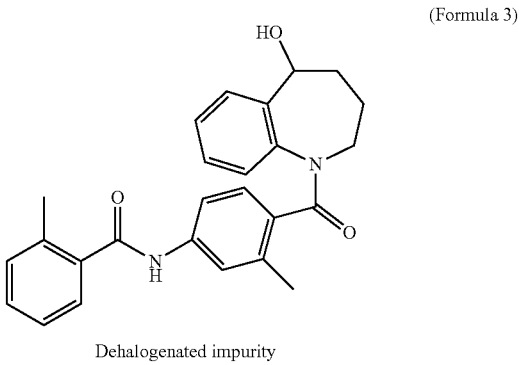 [SMILES: Cc1ccccc1C(=O)Nc1ccc(C(=O)N2CCCC(O)c3ccccc32)c(C)c1]

Dehalogenated impurity

Process for the preparation of Tolvaptan was reported in Bioorganic & medicinal chemistry 7 (1999, 1743-1754). According to the journal, Tolvaptan of Formula 1 is prepared from starting material of Formula 2 in 30% yield, as shown in the scheme below:

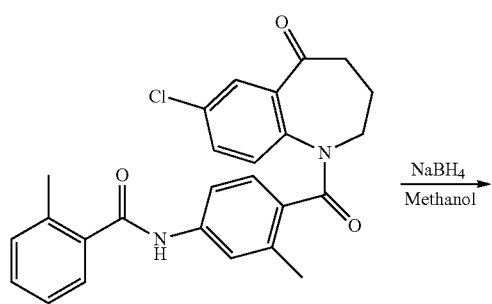

Formula 2

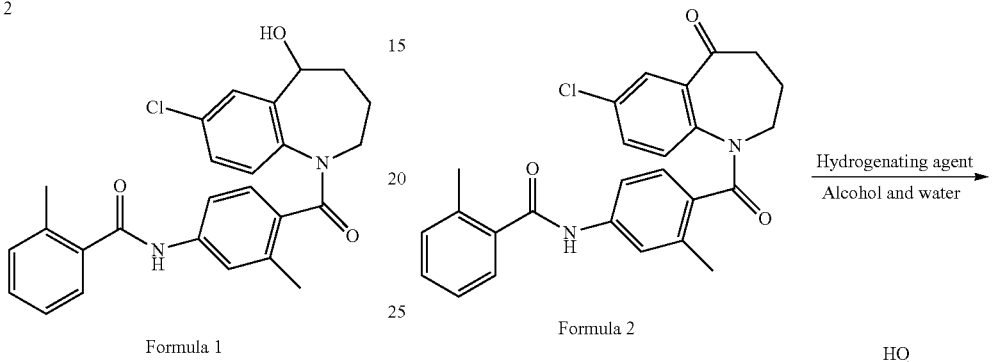

Formula 1

In this process, the solvent used is methanol and sodium borohydride is used as hydrogenating agent in an amount of 1.5 moles per 1 mole of starting material of Formula 2. The purity of the product is not mentioned in the journal but low yield (30%) makes this process industrially non-viable.

The low yield in chemical process is due to incomplete conversion of reactants into product and/or due to, formation of side products or impurities. Torisawa et al. suggests use of excess amount of sodium borohydride as hydrogenating agent leading to formation of impurities as drawback of the journal's process.

Also, the prior art processes involving use of hydrogenating agent are exothermic in nature suffering from temperature rise, which are not industrially safe. The inventors of the present invention have meticulously devised an industrially safe, feasible and efficient process for the preparation of Tolvaptan (Formula 1) in which conversion of starting material of Formula 2 to Tolvaptan is carried out in alcoholic solvent containing water. Presence of water in reaction mixture helps in controlling temperature rise during the reaction making it industrially safe.

SUMMARY OF THE INVENTION

The present invention provides novel, safe, industrially feasible and efficient process for the preparation of Tolvaptan (Formula 1) from 7-chloro-1-[2-methyl-4-(2-methyl benzoyl amino) benzoyl]-5 oxo-2,3,4,5-tetrahydro-1H-1-benzazipine (Formula 2) with high yield.

Another aspect of the present invention provides a process for the preparation of Tolvaptan obtained by reducing starting material of Formula 2 using a hydrogenating agent in a solvent mixture containing alcohol and water. During the process reaction, the temperature rise is controlled by presence of water in the reaction mixture. The percentage of water in the solvent mixture used in the present invention is in the range of 5% to 30%, more preferably in the range of 10% to 20%.

Yet another aspect of the present invention provides a process for the preparation of Tolvaptan having less than 0.1% of dehalogenated side product of Formula 3.

DETAILED DESCRIPTION OF THE INVENTION

The present invention provides an industrially safe, feasible and efficient process for the preparation of Tolvaptan of Formula 1 from starting material of Formula 2, as shown in the scheme below:

In a preferred embodiment of the present invention, starting material 7-chloro-1-[2-methyl-4-(2-methylbenzoylamino) benzoyl]-5-oxo-2,3,4,5-tetrahydro-1H-1-benzazepine of Formula 2 is reduced using hydrogenating agent in a solvent mixture containing alcohol and water to obtain Tolvaptan of Formula 1.

The starting material 7-chloro-1-[2-methyl-4-(2-methylbenzoylamino) benzoyl]-5-oxo-2,3,4,5-tetrahydro-1H-1-benzazepine of Formula 2 can be prepared in many different ways as thoroughly reported and taught in prior art literature.

The starting material of Formula 2 is suspended in solvent mixture of alcohol and water and hydrogenating agent is added in an amount of about 0.75 to about 2.0 moles, more preferably 1.2 to 1.4 moles per 1 mole of starting material The solid obtained is isolated by conventional technique, for example, by cooling the reaction mixture, filtering, concentrating and extracting the product etc.

The hydrogenating agent used in the present invention is selected from the group comprising of lithium borohydride, sodium borohydride, zinc borohydride and potassium borohydride, The hydrogenating agent is preferably sodium borohydride.

The solvent mixture containing alcohol and water used in the present invention is taken in proportion such that the percentage of water in the solvent mixture is in the range of 5% to 30%. During the process, the temperature rise is controlled due to presence of water in the reaction mixture, The alcohol used in the present invention is at least one solvent selected from the group comprising of methanol, ethanol, n-propanol, isopropanol and t-butanol. The solvent is preferably methanol.

In one preferred embodiment of the present invention, sodium borohydride is used as hydrogenating agent and is added in amount of about 0.75 to about 2.0 moles, more preferably about 1.2 to about 1.4 per 1 moles of starting material of Formula 2.

The process of the present invention gives Tolvaptan of more than 80% product yield and dehalogenated side product of Formula 3 of less than 0.1%, which is within regulatory guidelines specific stringent limits for impurities in drug substance (ICH-Q3A (R2)).

In another preferred embodiment, starting material of Formula 2 is reduced using sodium borohydride in a solvent mixture of methanol and water to obtain Tolvaptan of more than 80% product yield. The methanol and water in process are taken in proportion such that the percentage of water in the solvent mixture is in the range of 5% to 30%. More preferably, it is in the range of 10% to 20%. During the process, the temperature rise is controlled due to presence of water in the reaction mixture.

Further, acid may be added on completion of reaction to neutralize excess alkalinity. Hydrochloric acid or any other suitable mineral acid can be used for this purpose. The solid obtained is isolated by conventional technique, for example, by cooling the reaction mixture, filtering, concentrating and extracting the product.

Hereinafter, the present invention will be described in more detail with reference to the following examples. These examples are provided only for illustrating the present invention and should not be construed as limiting the scope and spirit of the present invention.

EXAMPLE 1

Preparation of 7-chloro-5-hydroxy-1-[2-methyl-4-(2-methylbenzoylamino) benzoyl]-2,3,4,5-tetrahydro-1H-1-benzazepine (Tolvaptan)

7-chloro-1-[2-methyl-4-(2-methyl benzoyl amino) benzoyl]-5 oxo-2,3,4,5-tetrahydro-1H-1-benzazepine (6.5 gm.) was suspended in methanol (104 ml) & water (10.4 ml) and then added sodium borohydride (0.385 gm.) at 30° C. and the reaction mixture was stirred for 1 hr. To the reaction mixture was added hydrochloric acid (39 ml). Then the reaction mixture was stirred for 2 hours. The solid obtained was collected by filtration and dried to give 7-chloro-5-hydroxy-1-[2-methyl-4-(2-methyl benzoyl amino) benzoyl]-2,3,4,5-tetrahydro-1H-1-benzazepine (5.8 gm.).

Yield—89.23%; Purity (HPLC)—99.85%; Dehalogenated Impurity—0.01%

EXAMPLE 2

Preparation of 7-chloro-5-hydroxy-1-[2-methyl-4-(2-methylbenzoylamino) benzoyl]-2,3,4,5-tetrahydro-1H-1-benzazepine (Tolvaptan)

7-chloro-1-[2-methyl-4-(2-methyl benzoyl amino) benzoyl]-5 oxo-2,3,4,5-tetrahydro-1H-1-benzazepine (25 gm.) was suspended in methanol (600 ml) & water (180 ml) and then added sodium borohydride (2.95 gm.) at 25° C. and the reaction mixture was stirred for 1hr. To the reaction mixture was added hydrochloric acid (150 ml). Then the reaction mixture was stirred for 2 hours. The solid obtained was collected by filtration and dried to give 7-chloro-5-hydroxy-1-[2-methyl-4-(2-methyl benzoyl amino) benzoyl]-2,3,4,5-tetrahydro-1H-1-benzazepine (22.8 gm).

Yield—91.2%; Purity (HPLC)—98.92%; Dehalogenated Impurity—0.01%

EXAMPLE 3

Preparation of 7-chloro-5-hydroxy-1-[2-methyl-4-(2-methylbenzoylamino) benzoyl]-2,3,4,5-tetrahydro-1H-1-benzazepine (Toivaptan)

7-chloro-1-[2-methyl-4-(2-methyl benzoyl amino) benzoyl]-5 oxo-2,3,4,5-tetrahydro-1H-1-benzazepine (2 gm.) was suspended in n-propanol (80 ml) & water (12 ml) and then added sodium borohydride (0.253 gm.) at 35° C. and the reaction mixture was stirred for 1 hr. To the reaction mixture was added hydrochloric acid (12 ml). Than the reaction mixture was stirred for 1 hour. The solid obtained was collected by filtration and dried to give 7-chloro-5-hydroxy-1-[2-methyl-4-(2-methyl benzoyl amino) benzoyl]-2,3,4,5-tetrahydro-1H-1-benzazepine (1.65 gm).

Yield—82.5%; Purity (HPLC)—99.73%; Dehalogenated Impurity—0.01%

EXAMPLE 4

Preparation of 7-chloro-5-hydroxy-1-[2-methyl-4-(2-methylbenzoylamino) benzoyl]-2,3,4,5-tetrahydro-1H-1-benzazepine (Toivaptan)

7-chloro-1-[2-methyl-4-(2-methyl benzoyl amino) benzoyl]-5 oxo-2,3,4,5-tetrahydro-1H-1-benzazepine (2 gm) was suspended in methanol (48 ml) & water (12 ml) and then added sodium borohydride (0.236 gm.) at 25° C. and the reaction mixture was stirred for 1hr. To the reaction mixture was added water (12 ml) and stirred for 2 hours at 25-30° C. The solid obtained was collected by filtration and dried to give 7-chloro-5-hydroxy-1-[2-methyl-4-(2-methylbenzoylamino) benzoyl]-2,3,4,5-tetrahydro-1H-1-benzazepine (1.70 gm).

Yield—85%; Purity (HPLC)—99.65%; Dehalogenated Impurity—below detection level

EXAMPLE 5

Preparation of 7-chloro-5-hydroxy-1-[2-methyl-4-(2-methylbenzoylamino) benzoyl]-2,3,4,5-tetrahydro-1H-1-benzazepine (Tolvaptan)

7-chloro-1-[2-methyl-4-(2-methyl benzoyl amino) benzoyl]-5 oxo-2,3,4,5-tetrahydro-1H-1-benzazepine (5 gm,) was suspended in methanol(40 ml) & water (6 ml) and then added sodium borohydride (0.211 gm.) at 30° C. and the reaction mixture was stirred for 1 hr. To the reaction mixture was added hydrochloric acid (30 ml). Then the reaction mixture was stirred for 2 hours, The solid obtained was collected by filtration and dried to give 7-chloro-5-hydroxy-1-[2-methyl-4-(2-methyl benzoyl amino) benzoyl]-2,3,4,5-tetrahydro-1H-1-benzazepine (4.55 gm).

Yield—91%; Purity (HPLC)—99.08%; Dehalogenated Impurity—0.03%

Comparative Study of Reaction Exotherm Using Reaction Calorimeter

Example 6

Preparation of 7-chloro-5-hydroxy-1-[2-methyl-4-(2-methylbenzoylamino) benzoyl]-2,3,4,5-tetrahydro-1H-1-benzazepine (Tolvaptan) Using Methanol as a Solvent 7-chloro-1-[2-methyl-4-(2-methyl benzoyl amino) benzoyl]-5 oxo-2,3,4,5-tetrahydro-1H-1-benzazepine (18.75 gm.) was suspended in methanol (150 ml) and then added sodium borohydride (2.23 gm.) at 26° C. There was temperature rise of 37° C. The reaction temperature rose to 63° C.

EXAMPLE 7

Preparation of 7-chloro-5-hydroxy-1-[2-methyl-4-(2-methylbenzoylamino) benzoyl]-2,3,4,5-tetrahydro-1H-1-benzazepine (Tolvaptan) Using Methanol and Water as a Solvent 7-chloro-1-[2-methyl-4-(2-methyl benzoyl amino) benzoyl]-5 oxo-2,3,4,5-trahydro-1H-1-benzazepine (15 gm.) was suspended in methanol (120 ml) & water (28.8 ml) and then added sodium borohydride (1.78 gm.) at 26° C., There was temperature rise of 15° C. The reaction temperature rose to 41° C.

The invention claimed is:

1. A process for the preparation of Tolvaptan comprising reducing (7-chloro-1-[2-methyl-4-(2-methylbenzoylamino) benzoyl]-5-oxo-2,3,4,5-tetrahydro-1H-1benzazepine) of Formula 2

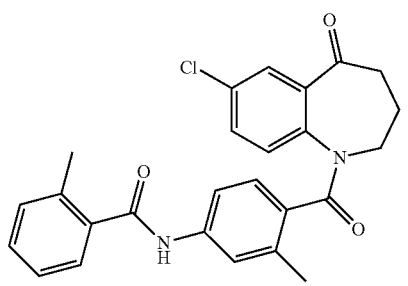

Formula 2 using a hydrogenating agent selected from the group comprising of lithium borohydride, sodium borohydride, zinc borohydride, and potassium borohydride in a solvent mixture comprising an alcohol selected from the group comprising of methanol, ethanol, n-propanol, isopropanol and t-butanol and water, wherein the percentage of water in the solvent mixture is 5% to 30%.

2. The process as claimed in claim 1, wherein the hydrogenating agent is sodium borohydride.

3. The process as claimed in claim 1, wherein the alcohol is methanol.

4. The process as claimed in claim 1, wherein the percentage of water in the solvent mixture is 10% to 20%.

5. The process as claimed in claim 1, wherein the hydrogenating agent is in amount from about 0.75 to about 2.0 moles per 1 mole of starting material of Formula 2.

6. The process as claimed in claim 1, wherein the hydrogenating agent is in amount from about 1.2 to about 1.4 moles per 1 mole of starting material of Formula 2.

7. The process as claimed in claim 1, wherein a temperature rise of the process is controlled by water present in the reaction mixture.

8. Tolvaptan obtained by a process of claim 1, wherein the Tolvaptan contains less than 0.1% of a dehalogenated impurity of Formula 3

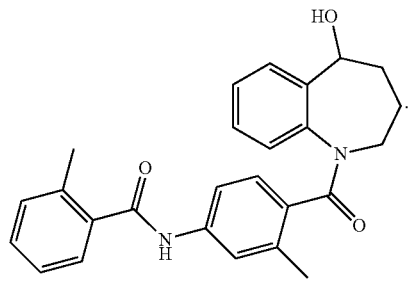

Formula 3

* * * * *